(12) United States Patent
Papavinasam et al.

(10) Patent No.: US 6,673,222 B1
(45) Date of Patent: Jan. 6, 2004

(54) BIOLOGICAL ACTIVITY PROBE

(75) Inventors: Sadaksharasundaram S. Papavinasam, Nepean (CA); William D. Gould, Ottawa (CA); Robert W. Revie, Ottawa (CA); Fraser A. MacLeod, Ottawa (CA); Michael Attard, Ottawa (CA)

(73) Assignee: Her Majesty the Queen in Right of Canada, as represented by the Minister of Natural Resources, Ottawa (CA)

( * ) Notice: Subject to any disclaimer, the term of this patent is extended or adjusted under 35 U.S.C. 154(b) by 398 days.

(21) Appl. No.: 09/809,108

(22) Filed: Mar. 16, 2001

(51) Int. Cl.$^7$ ............................................ G01N 27/327
(52) U.S. Cl. .................. 204/404; 204/416; 204/403.14; 204/431
(58) Field of Search .............................. 204/416, 403.14, 204/431, 404; 205/775, 786.5, 775.5

(56) References Cited

U.S. PATENT DOCUMENTS

| | | |
|---|---|---|
| 4,999,286 A | 3/1991 | Gawel et al. |
| 6,113,762 A * | 9/2000 | Karube et al. ......... 204/403.06 |

OTHER PUBLICATIONS

Kubo et al. (Thiosulfate sensor based on *Thiobacillus thioparus*, Transactions of the Materials Research Society of Japan (1994), 15A (Biomaterials, Organic and Intelligent Materials), 477–80).*

Handbook of Microbiological Media By Ronald M. Atlas; Ed. L.C.Parks, CRC Press, p. 896. (The copy is not dated; published before Mar. 16, 2001.).

Manual of Methods for General Bacteriology, Ed. P. Gerhardt, American Society for Microbiology, Washington D.C., 1981, pp. 155–156.

Biosensors; C. Crabb, Chemical Engineering, 1998, pp35–39.

Determination of Aqueous Sulfide . . . ; Lindsay et al, in Ground Water Contamination: Field Method ASTM Special Technical Publication 936, Ed A.G.Collins; ASTM, Philadelphia, PA, 1986, pp 349–357.

Biosensors: Principles of Operation . . . ; Nwosu et al., Bulletin of Electrochemistry 8 (5) 239–255(1992).

Purification . . . of Methyl Mercaptan Oxidase from *T. thioparus* TK–m; Gould et al.; J. General Microbiology, 138, 217–221 (1992).

Biosensors; Guilbault, Current Opinion in Biotechnology, 2, 3–8(1991).

(List continued on next page.)

*Primary Examiner*—Alex Noguerola
(74) *Attorney, Agent, or Firm*—Robert A. Wilkes; Shapiro Cohen

(57) ABSTRACT

A biological activity probe for the detection on-line of the presence of sulphide including an enzyme electrode; a counter electrode; a reference electrode; and if desired a corrosion electrode. The enzyme electrode includes an immobilised source of sulfide oxidase enzyme, together with a cofactor such as 1,1'-dimethylferrocene, immobilised in a water permeable non-conducting binder on a biologically inert electrically conducting substrate. The immobilised source of sulfide oxidase enzyme is either a chemoautotropic microorganism such as a *Thiobacillus thioparus*, or enzyme material recovered from a culture of a *Thiobacillus thioparus*. The probe when connected to a suitable electrical system is capable of identifying microbiological activity resulting in microbiologically influenced corrosion; microbiological activity not resulting in microbiologically influenced corrosion; microbiological inactivity, coupled with non-microbiologically influenced corrosion; and microbiological inactivity; and no corrosion.

11 Claims, 4 Drawing Sheets

Monitoring SRB Activity

OTHER PUBLICATIONS

Electrode Sytems for . . . Cardiovascular Surgery; Clark, Jr., et al., Ann. N. Y. Acad. Sci.,102, 29–45, 1962.

Jun. 3, 1967, The Enzyme Electrode; Updike et al, Nature, 214, 986–988, 1967.

Enzyme Electrode Biosensors; Kauffmann et al., Bioanalyatical Applications of Enzymes, 36, 64–113, 1992.

A New Approach to ImmunoFET Operation; Kooyman et al., Biosensors & Bioelectronics, 5, 103–124 (1990).

Surface Acoustic Wave Sensor Response . . . ; Heckl et al., Anal. Chem. 62, 32–37 (1990).

Feasibility of using fiber optics . . . ; Hirschfeld et al., Optical Engineering, 22, 527–531 (1983).

Enzyme Electrodes; Coulet, GBF Monographs, 10, 75–80 (1987).

Pyruvate and Lactate Electrochemical Sensors; Mascini et al.; Ann. Di Chim. 77,813–824 (1987).

USe of an Enzyme Thermistor; Hundeck et al., Dechema Biotechnology Conferences 3, 1989.

Corrosion of Mild Steel under Anaerobic Biofilm; lee et al., Corrosion, 49, 186–199 (1993).

Mitigation Strategies for Microbiologically Influenced Corrosion; Pope et al.; Corrosion 89, Paper 192, New Orleans, 1989.

External Corrosion of Line Pipe; Kack et al., Biologically Induced Corrosion; Proc. Int. Conf., Houston, 1985, pp 339–350.

Biology of Microorganisms; Ed. Brock et al., $4^{th}$. Edn, pp 702–707.

Photomicrobial electrode for . . . selective determination of Sulphide; Matsunaga et al., Applied and Microbiology Technology, 19, 404–408 (1984).

Microbial Sensor for . . . selective determination of Sulphide; Kurosawa et al., Applied Microbiology Technology, 41, 558–559 (1994).

New Enzyme Sensor for Sulfite Analysis; Campanella et al., Analytica Chimica Acta, 305, 32–41 (1995).

Microbial Sensor . . . ; for Determination of Sulfite in Wires Kawamura et al., J. AOAC International, 77, 1052–1056 (1994).

Testing for the Presence of Sulfate Reducing Bacteria; Tatnall et al., Materials Performance, 8, 71–80 (1988).

A Biosensor base on *T. thioparus* for measuring thiosulfate and methanethiol; Kubo et al., Cn. J. Microbiol. 41.

* cited by examiner

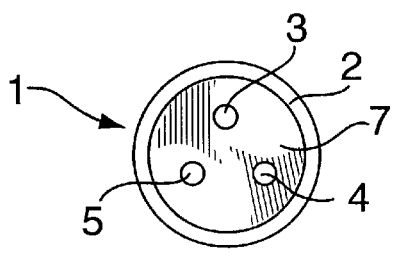
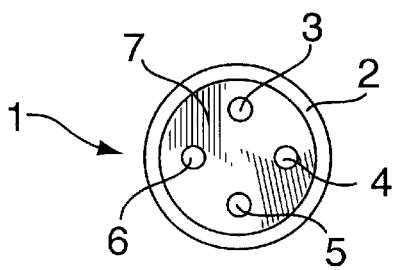
FIG. 1  FIG. 2
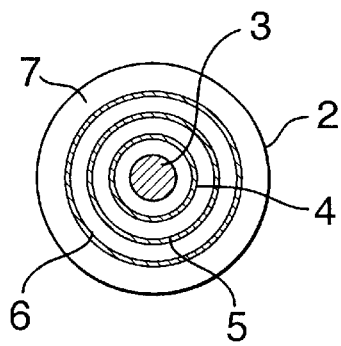
FIG. 3
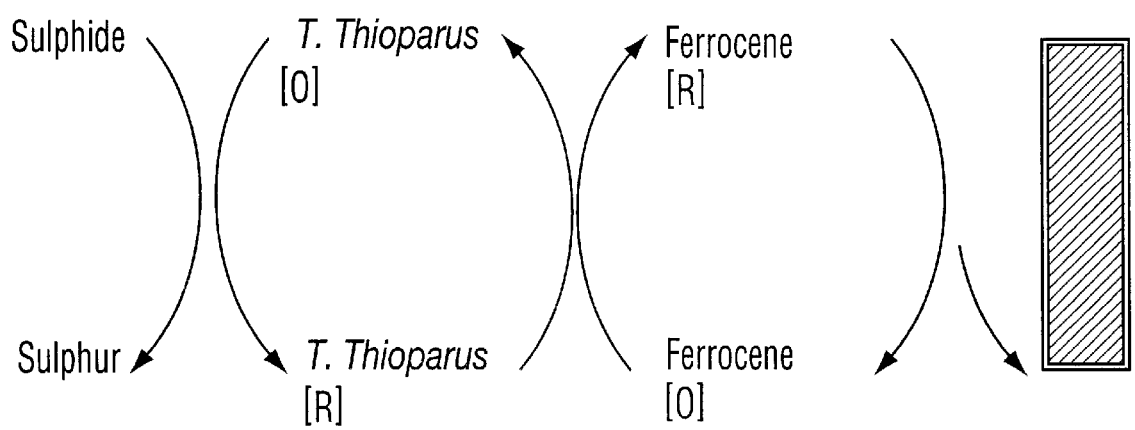
FIG. 4

BIOLOGICAL ACTIVITY PROBE

TECHNICAL FIELDS

This invention relates to a biological activity probe for the detection on-line of the presence of sulphide. It is thus applicable for the detection of a level of microbiological activity involving sulphide which is likely to influence corrosion, for example of a buried metal pipeline, or to result in the formation of biofilm surface coatings, for example inside either metallic or non-metallic pipes. The probe is thus of use in monitoring biological activity both inside and outside a number of structures, such as buried pipelines, and heat exchanger structures.

BACKGROUND ART

Since the discovery of sulphate reducing bacteria by Bijerninck in 1905, microbiologically influenced corrosion has been the subject of considerable interest. Microbiologically influenced corrosion has been documented for metals, particularly ferrous metals, exposed to seawater, fresh water, water associated with crude oil and with natural gas, demineralised water, chemical process flows, foods, aircraft fuels, human plasma, and sewage. Despite the evidence that the presence of a number of different groups of microorganisms can influence and accelerate rates of corrosion, sulphide producing microorganisms, including sulphate reducing bacteria (SRB), have received the most attention as the causative, agents of microbiologically influenced corrosion for a number of reasons. In addition to being the most common causative group of microorganisms involved in microbiologically influenced corrosion, they were identified as being involved in the first corrosion mechanism that accounted for anaerobic corrosion of ferrous metals. In a suitable environment, sulphate reducing bacteria will produce sulphide ions, typically as hydrogen sulphide, which will corrode metals, including ferrous metals, copper, and nickel alloys.

A parallel problem resulting from the presence of active bacteria is the formation of adherent coatings of biofilm on a wide variety of surfaces, which includes the surfaces of both metallic and non-metallic materials, such as the inside of metal and plastic pipes. The formation of an internal biofilm obstructs the pipe bore and thus impairs its flow capacity, and in applications such as heat exchangers can significantly degrade pipe heat exchange properties.

Although the involvement of sulphide producing microorganisms (e.g. SRB) in microbiologically influenced corrosion is well known, and conditions have been identified that are suitable for the growth of sulphide producing bacteria, analytical methods are still lacking which will provide definitive indicators that microbiologically influenced corrosion in fact will occur. For example, there does not appear to be any consistent correlation between the size of a population of sulphate reducing bacteria present in a given environment, and the microbiologically influenced corrosion in that environment. Further, at present there are no definitive tests available that can be used on line for a structure in the field to detect microbiologically influenced corrosion, although there are some features of the results of microbiologically influenced corrosion which have been identified, such as non-uniform pitting, pits filled with black corrosion products, round pits under tubercles in carbon steel, and pinholes leading to large subsurface cavities in stainless steel. Consequently, in the absence of definitive and reliable indicators, identification of the presence of conditions which will foster microbiologically influenced corrosion is difficult.

In the past, three approaches have been proposed as a means to monitor conditions which can be taken to indicate that microbiologically influenced corrosion might be occurring. These are to monitor the relative quantity of microorganisms that are present, to monitor microbiological influences, and to monitor on-going corrosion.

In order to monitor the number of organisms present, techniques utilising more or less conventional culturing procedures have been used, with both an iron source and sulphate ions being included in the culture medium. If sulphate reducing bacteria are present, black ferrous sulphide is formed. The number of positive samples in a most probable number method can be used to assess the quantity of sulphate reducing bacteria that are present. Alternatively, several direct methods for detecting the presence of sulphide producing microorganisms have been proposed. In these methods, the method does not require the growth of microorganisms during the test. Instead, after removal of dissolved solids that might interfere with the test, a photochemical procedure, usually involving enzymatic reduction, is used.

In order to monitor microbiological influences, several indirect methods have been proposed. The presence of an adhering biofilm on a metallic surface alters the properties of that surface, and can also modify the local anodic and cathodic processes. For example, the simple presence of a biofilm will alter the pressure drop through an orifice, and will alter the heat transfer properties of a tube surface, provided that there is enough biofilm formation to provide meaningful results.

In order to monitor on-going corrosion, several procedures have been proposed, which seek to provide an alert that the metallic system is corroding, and at what rate. Commonly used methods include weight loss coupons, galvanic probes, electrochemical probes and system simulations.

These proposed systems all however suffer from several significant disadvantages.

Although the biological procedures are capable of indicating that sulphide producing microorganisms are present, and often an indication of the relative size of the sampled population, these methods give no information at all as to whether microbiologically influenced corrosion might be actually happening. Furthermore, the biological procedures are only useable on a relatively small scale and in a laboratory environment; they are not capable of being used on line in the field to monitor any activity in the environment of a structure.

Although the measurements of microbiological presence are sometimes capable of detecting physical changes, such as the consequences of biofilm formation, these methods too do not indicate whether microbiologically influenced corrosion is either likely to happen or even happening. For example, a reduction in the heat transfer properties of a tube only indicates that a biofilm is likely to be present, and cannot give any useful information about the bacteria in that biofilm.

Although corrosion monitoring methods provide information on total corrosion rates, these methods do not provide any information on either whether the corrosion includes any microbiologically influenced corrosion, or the relative rate of any microbiologically influenced corrosion if it is occurring.

Thus although microbiologically influenced corrosion has been invoked as the cause of many unexpected corrosion failures, typically of buried steel pipes, evidence identifying microbiological activity as the primary cause of the failure continues to be elusive. There is no currently available technique that can be used to characterise a microbial population in the field, and that can provide useful information about the potential microbiologically influenced corrosion risks to which a given structure is exposed.

BRIEF SUMMARY OF THE INVENTION

This invention seeks to provide a biological activity probe for monitoring microbiological activity in the environment of a structure, to detect the presence of microorganisms which to produce substances such as sulphides which are known to have a direct influence on corrosion. The probe of this invention can be used to detect the activity of sulphide producing microorganisms (e.g. SRB's ) both in situ and on line on a real time basis. In a preferred embodiment, the probe can provide information on corrosion conditions. The probe can be used to detect the activity of microorganisms such as anaerobic sulphide producing microorganisms e.g. SRB), and is believed to function also under aerobic conditions.

Thus in a first embodiment this invention seeks to provide a probe for monitoring the activity of sulphide producing microorganisms including:

(1) an enzyme electrode;
(2) a counter electrode; and
(3) a reference electrode;
   which are all connectable to a suitable electrical system for data acquisition, wherein:
      the enzyme electrode comprises an immobilised source of sulfide oxidase enzyme, together with a cofactor, immobilised in a water permeable non-conducting binder on a biologically inert electrically conducting substrate;
      the cofactor comprises an artificial mediator that replaces oxygen under anaerobic conditions;
      the counter electrode comprises a biologically inert electrically conducting electrode; and
      the reference electrode comprises a biologically inert electrically conducting electrode.

In a second embodiment this invention seeks to provide a probe for monitoring the activity of sulphide producing microorganisms in the environment of a structure incorporating a metal including:

(1) an enzyme electrode;
(2) a counter electrode;
(3) a reference electrode; and
(4) a corrosion electrode;
   which are all connectable to a suitable electrical system for data acquisition, wherein:
      the enzyme electrode comprises an immobilised source of sulfide oxidase enzyme, together with a cofactor, immobilised in a water permeable non-conducting binder on a biologically inert electrically conducting substrate;
      the cofactor comprises an artificial mediator that replaces oxygen under anaerobic conditions;
      the counter electrode comprises a biologically inert electrically conducting electrode;
      the reference electrode comprises a biologically inert electrically conducting electrode; and
      the corrosion electrode comprises a metal electrode.

Preferably, the immobilised source of sulphide oxidase enzyme comprises a chemoautotropic microorganism.

Preferably, the chemoautotropic microorganism is a *Thiobacillus thioparus* species. Alternatively, the immobilised source of sulphide oxidase enzyme comprises enzymatic material recovered from a culture of a *Thiobacillus thioparus* species.

Preferably, the cofactor is chosen from the group consisting of pyocyanine, phenazine metasulphate, 1,2-naphthoquinone, 2,6-dichlorophenolindophenol, tetracyanoquinodimethane, 1,4-benzoquinone, the compound $Ru(NH_3)_5pyridinium(PF_6)$, chlornil, potassium ferricyanide, N,N,N',N'-tetramethyl-p-phenylenediamine, ferrocene monocarboxylic acid, tetrathiafulvene, ferrocene and 1,1'-dimethyl ferrocene. More preferably, the cofactor is chosen from 1,1'-dimethylferrocene and ferrocene. Most preferably, the cofactor is 1,1'-dimethylferrocene.

Conveniently, the counter electrode, the reference electrode and the corrosion electrode if present are the same.

Preferably, the counter electrode is chosen from the group consisting of a graphite electrode, a stainless steel electrode, and a steel electrode.

Preferably, the reference electrode is chosen from the group consisting of a graphite electrode, a stainless steel electrode, a carbon steel electrode; a standard calomel electrode (SCE), a copper/copper sulphate electrode, and a silver/silver chloride electrode.

Preferably, the electrodes are mounted within a protective outer shell having an opening at its first end for the electrode active surfaces, and having provision for electrical connections to the electrodes at its second end, and the electrodes are separated from each other within the shell by a biologically inert insulating material.

The probe of this invention thus relies on the enzymatic oxidation of sulphide, which requires the presence of a sulphur oxidase enzyme. In the context of a probe, this can be achieved in two ways: either the probe includes a suitable amount of an immobilised chemoautotropic microorganism, such as a *Thiobacillus thioparus*, or the probe includes a suitable amount of a sulphur oxidase enzyme, such as an active enzyme concentrate derived from a *Thiobacillus thioparus*. For each of these options the construction of the probe for either laboratory or for field use is more or less the same, the chief differences being the active material which is immobilised on the enzyme electrode, and the technique used to prepare the active material. For either option, a suitable microorganism source material is required.

BRIEF DESCRIPTION OF THE DRAWINGS

The invention will now be described with reference to the attached drawings in which:

FIGS. 1 and 2 show schematically end-on views of a first arrangement for the electrodes in a probe for field use;

FIG. 3 shows an alternative electrode arrangement to FIG. 2;

FIG. 4 shows schematically the operation of the enzyme electrode;

DETAILED DESCRIPTION OF THE INVENTION

Figure 5:
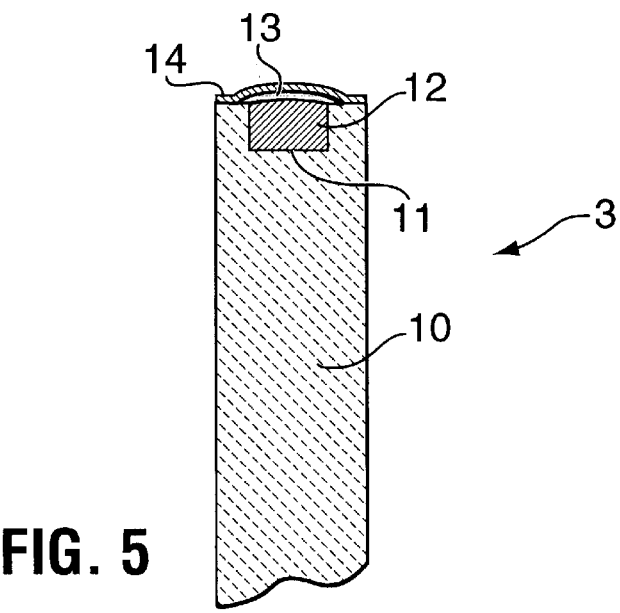
FIG. 5 shows schematically a typical construction for the enzyme electrode.

Referring first to FIG. 1 the biological activity probe 1 includes three electrodes within a casing 2. These are an enzyme electrode 3, a reference electrode 4, and a counter electrode 5. In FIG. 2 the construction is essentially the same as that in FIG. 1, with the addition of a fourth corrosion electrode 6. In the constructions shown in both of FIGS. 1 and 2, and in the alternative construction shown in FIG. 3 which is discussed in more detail below, the electrodes 3, 4 and 5, and a corrosion electrode 6 if present, are held in place by a body of insulating plastic material 7, typically a phenolic or epoxy resin as used in other electronics applications.

In FIG. 3 an alternative arrangement is shown in which four concentric electrodes are used. The outer casing 2, electrical connections, and the insulation 7 between the electrodes are the same as in FIGS. 1 and 2. The enzyme electrode 3 is at the centre, with the reference electrode 4, the counter electrode 5 and the corrosion electrode 6 as a set of concentric rings around it. Since the electrical measurements can be influenced by the exposed surface area of the electrodes, it is convenient to fabricate the probe with the exposed surface areas of each of the reference electrode 4, the counter electrode 5, and the corrosion electrode 6 substantially the same. If they are not all the same, the surface area of at least the corrosion electrode 6 needs to be known in order to calculate corrosion rate data. As is shown in FIGS. 1 and 2, the corrosion electrode 6 is optional and can be omitted.

The material used for the casing 2 will depend to some extent on the environment in which the probe is to be used; an engineering plastic material such as polyamide or ABS, which can be fibre reinforced if desired, will generally be found suitable. The other end of the casing 2 (not shown) is constructed to accommodate a sealed connection from the electrodes to a cable used for data retrieval. Suitable cables and connections for them are well known; for field use a sealed and protected cable is preferred. How the connections are made to each electrode will depend on the construction of the electrode; for example techniques for making an electrical connection to the graphite used in the enzyme electrode are well known. The presence of the corrosion electrode 6 is optional, as will be discussed in more detail below.

In FIGS. 1, 2 and 3 the construction shown is intended primarily for field use. For laboratory use the casing 2 and the insulation 7 can be omitted if desired, and each electrode suitably separately supported.

The enzyme electrode includes either a suitable amount of an immobilised chemoautotropic microorganism, such as a *T. thioparus species*, or a suitable amount of an immobilised sulphide oxidase enzyme, such as an active enzyme concentrate derived from a *T. thioparus*, together with a cofactor, immobilised in a water permeable non-conducting binder on a biologically inert electrically conducting substrate. FIG. 4 shows schematically an overview of the chemical reactions involved, using *T. thioparus* as the enzyme source and 1,1'-dimethylferrocene as the cofactor. The analysis for sulphide is carried out amperometrically, by applying a constant potential under anaerobic conditions, for example of about +0.3V relative to a standard calomel reference electrode, and monitoring the variation of current between the enzyme electrode and the counter electrode. At this potential, 1,1'-dimethylferrocene is oxidised electrochemically. Any sulphide ions present are oxidised by *T. Thioparus* to sulphur.

In order for this enzymatic reaction to occur, the presence of an electron acceptor such as 1,1'-dimethyl ferrocene as the 1,1'-dimethylferrocinium ion is required. During the enzymatic reaction, 1,1'-dimethyl ferrocene is produced. The oxidation current measured therefore will increase proportionally to the concentration of sulphide ions. Other electron acceptors can be used, which will also require a different applied voltage. Some examples of other suitable electron acceptors, together with their standard redox potential against a standard calomel electrode, are given in Table 1.

TABLE 1

| Electron Acceptor | Standard Redox Potential, vs. Standard Calomel Electrode |
| --- | --- |
| Pyocyanine | −240 mV |
| Phenazine Metasulphate | −160 mV |
| 1,2-Naphthaquinone | −90 mV |
| 2,6-Dichlorophenolindophenol | −15 mV |
| Tetracyanoquinodimethane | +6 mV |
| 1,4-benziquinone | +40 mV |
| Ru(NH$_3$)$_5$pyridinium(PF$_6$) | +50 mV |
| 1,1'-Dimethylferrocene | +100 mV |
| Chlornil | +100 mV |
| Ferrocene | +180 mV |
| Potassium Ferrocyanide | +190 mV |
| N,N,N',N'-Tetramethyl-p-phenylenediamine | +275 mV |
| Ferrocene Monocarboxylic Acid | 290 mV |
| Tetrathiafulvene | +340 mV |

The enzyme electrode can use *T. Thioparus* as the active chemoautotropic bacterium a suitable bacterium sample is available from the American Type Culture Collection, Rockland, Md., USA under accession number 23645, which can be propagated by known methods to provide a population for use in fabricating enzyme electrodes (see Handbook of Microbiological Media by R. M. Atlas, Ed. L. C. Parks, CRC Press, p. 896, and Manual of Methods for General Bacteriology, Ed. P Gerhardt, American Society for Microbiology, p. 155).

A typical construction for an enzyme electrode utilising immobilised *T. thioparus* invention is shown schematically in FIG. 5. The enzyme electrode 3 comprises a graphite rod 10, to one end of which an electrical connection is made(not shown) by conventional techniques. At the active end of the electrode, a depression 11 is provided for the immobilised *T. Thioparus*. The microorganism is mixed with 1,1'-dimethylferrocene, if desired together with some graphite paste, in a binder to provide suitable concentrations in the binder of both microorganism and 1,1'-dimethylferrocene. Although some experimentation may be necessary to obtain a mixture with desirable electrical properties, a typical mixture contains about 10 mg of *T. thioparus*, 3 mg of 1,1'-dimethylferrocene, and 100 mg of graphite powder together with sufficient binder to provide a thick paste. The binder has to be non-conducting, biologically inactive, and permeable to water, to provide a surface on which the bacterium can metabolise sulphide ions; a silicone binder, such as Fluka Silicone Oil DC 200 has been found to be suitable. A suitable amount 12 of the mixture including the immobilised *T. Thioparus* is packed into the depression 11, and sealed into it with a suitable surface coating 13, for which a thin coating of the silicone oil can be used. The immobilised microorganism paste is protected by covering it with a short length 14 of Fisherbrand dialysis tubing, available from Fisher Scientific, Pittsburgh, Pa., USA.

The reaction of an enzyme probe using *T. thioparus* as the enzyme source and 1,1'-dimethylferrocene as the cofactor was determined under laboratory conditions using the following procedure. A test cell was set up containing a phosphate buffer solution at pH 7 which had been deaerated for 24 hours by passing nitrogen through it; the deaerated buffer solution was pumped into the cell under nitrogen pressure. The other cell electrodes were a saturated calomel electrode (SCE) as the reference electrode, and a steel rod as the counter electrode. A potential of +0.3V vs the SCE was applied, and the current monitored as a function of time. After the observed current reached a steady stable value, 10 µL of ammonium sulphide was injected into the cell. A new steady state was reached, and another 10 µL of ammonium sulphide was injected into the cell. When a second new steady state was reached a third injection was made, and this sequence was repeated until 50 µL of ammonium sulphide had been injected into the cell.

Figure 6:
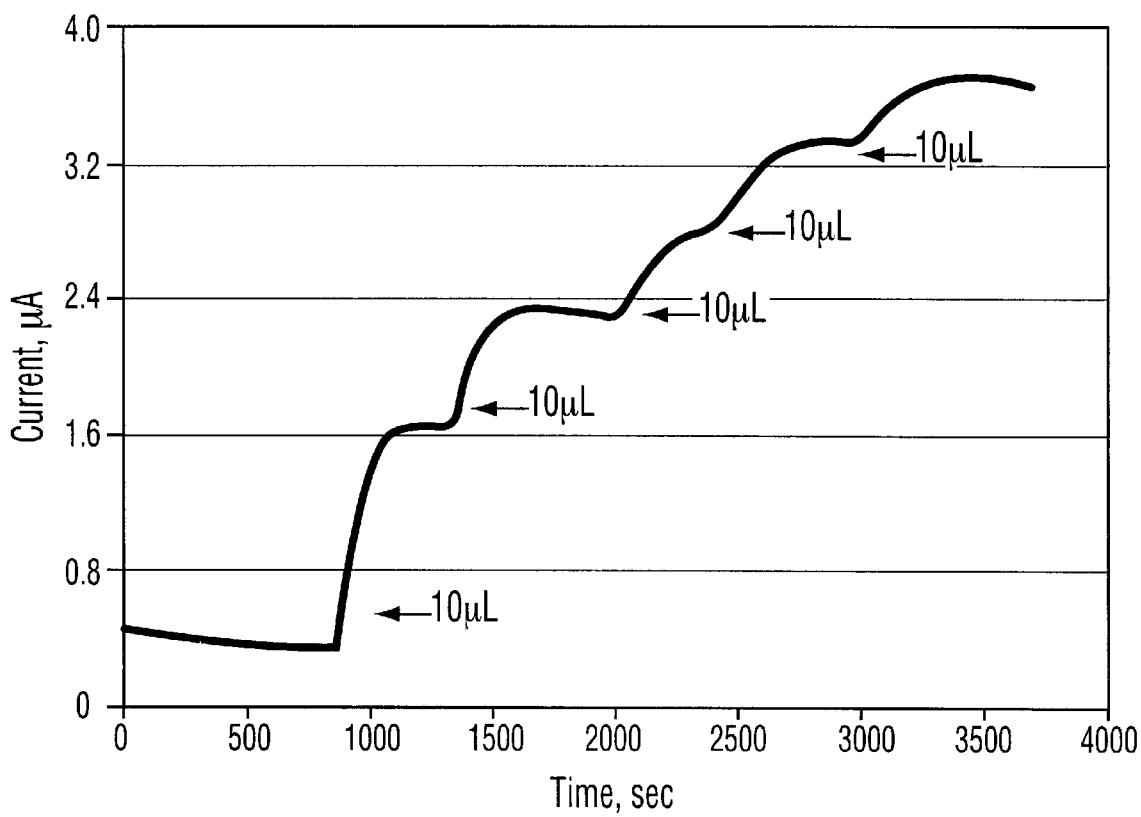
FIG. 6 shows the variation of observed probe current with sulphide concentration.

FIG. 6 shows the amperometric response of the test cell. The amperometric response is almost instantaneous, and is proportional to sulphide concentration.

In order to construct an enzyme electrode using immobilised enzyme, it is first necessary to isolate a suitable enzyme concentrate from, for example, a *T. thioparus*. A typical culturing and isolation procedure is as follows.

A culture of freeze dried *T. thioparus* was inoculated into a 250 ml Erlenmayer flask containing 100 ml of a sterile distilled water solution containing the following in g/L: 0.1g $NH_4Cl$; 3.0 g $KH_2PO_4$; 0.2 g $MgCl_2.6H_2O$; 5 g $Na_2S_2O_3.5H_2O$; and 0.1 g $CaCl_2$. The solution was adjusted to pH 7 with 6M NaOH. The flask was incubated on a rotary shaker at ambient temperature. The culture was transferred to a 2.8 L Erlenmeyer flask containing 1 L of the same medium and placed on a rotary shaker. Once a drop in pH was observed, the culture was fed by adding 0.5 g sodium sulfide dissolved in a small volume of sterile distilled water. The pH was monitored, and as required further aliquots of sodium sulphide were added, to maintain pH 7. The maximum amount of sodium sulphide added in a 24 hour period was 3.0 g regardless of the pH. Following feeding, the culture was returned to the shaker.

Cells were harvested by centrifugation(8,000 rpm, 20 min), resuspended in Tris-HCl buffer at pH 7.5, and centrifuged again. After resuspension in a minimum of supernatant, an ultrasonic homogeniser was used to disrupt the cells. An ice bath was used to cool the sample, and four periods of sonification were separated by three minutes cooling to ensure the sample did not overheat. The resulting paste was then centrifuged again(8,000 rpm) and the supernatant removed. The pellets were also recovered, and re-sonicated to recover any remaining enzyme material. The sulphide oxidase activity can be determined by the methylene blue method, under anaerobic conditions a plot can be made of optical density vs. a control, at 670 nm; sulphide concentration is determined by comparison with a standard curve generated with known sulphide concentrations. If desired, the sample protein content can be determined using the Sigma Diagnostics Micro Protein Determination Phenol Reagent Method for Biologic Fluids, Procedure No. 690. If desired, the sulphide oxidase preparation can be further purified by ultrafiltration, for example with a filter have a pore size of 50 kDa or of 100 kDa.

The enzyme can be immobilised in several ways for probe preparation. Once the enzyme is immobilised, it is preferably kept wet with water. All of the following have been found to be effective: physical entrapment between two membranes; entrapment with a dialysis membrane; physical entrapment onto a surface such as by immobilisation with glutaraldehyde onto a cellulose membrane; entrapment in polyvinyl alcohol; entrapment on graphite powder in a silicone oil paste; entrapment on graphite powder in a silicone oil paste including a cofactor, such as 1,1'-dimethylferrocene; and immobilisation with glutaraldehyde onto a cellulose membrane combined with a paste of graphite powder and silicone oil including a cofactor such as 1,1'-dimethylferrocene. Of these, entrapment on graphite powder in a silicone oil paste including 1,1'-dimethylferrocene is preferred.

Corrosion rates are derived from measurements made using the linear polarisation method. The open circuit potential is measured until it reaches a steady state value usually after about an hour. The linear polarisation measurement is obtained by scanning the potential between −20 mV and +20 mV with respect to the corrosion potential, at a scan rate of 0.1 mV/sec. After each scan, the open circuit potential is again monitored until it reaches a steady-state value. From the linear plot of current vs. potential the polarisation resistance $R_1$ is calculated; from this both the corrosion current, $I_{corr}$, and the corrosion rate in uA/cm² are derived. The relationships are:

$$I_{corr} = 0.0271/R_p \qquad 1.$$

$$8.8 \text{ uA/cm}^2 = 0.1 \text{ mm per year} \qquad 2.$$

It can thus be seen that the electrodes within the probe can be used in two sets for measurements. For biochemical activity, the enzyme, reference and counter electrodes are used; for corrosion rates, the reference, corrosion, and counter electrodes are used.

Corrosion rate, and activity of sulphide producing microorganisms activity, are monitored using conventional methods of data retrieval and management using a suitable controller, such as a computer with a display screen and adequate available memory.

Figure 7:
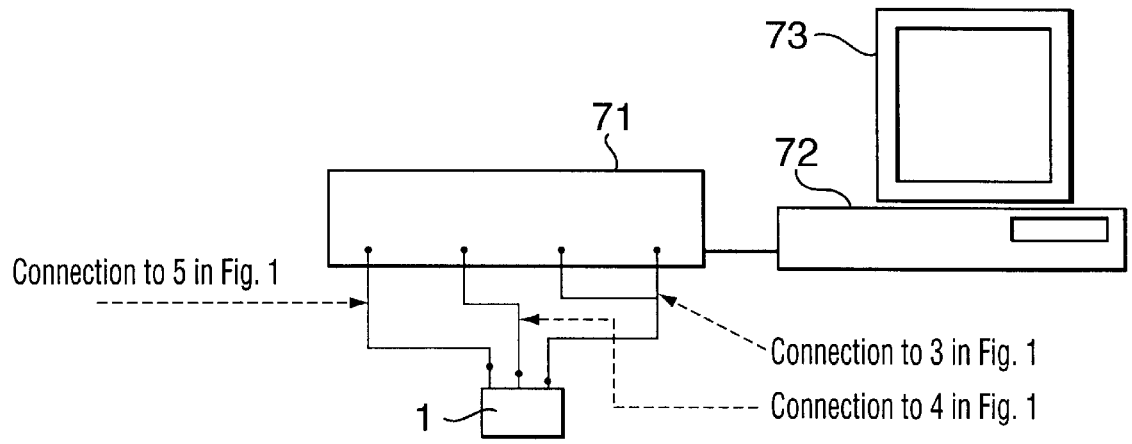
FIGS. 7 and 8 show schematic circuit diagrams for the measurements taken using the probe of FIG. 2.
Figure 8:
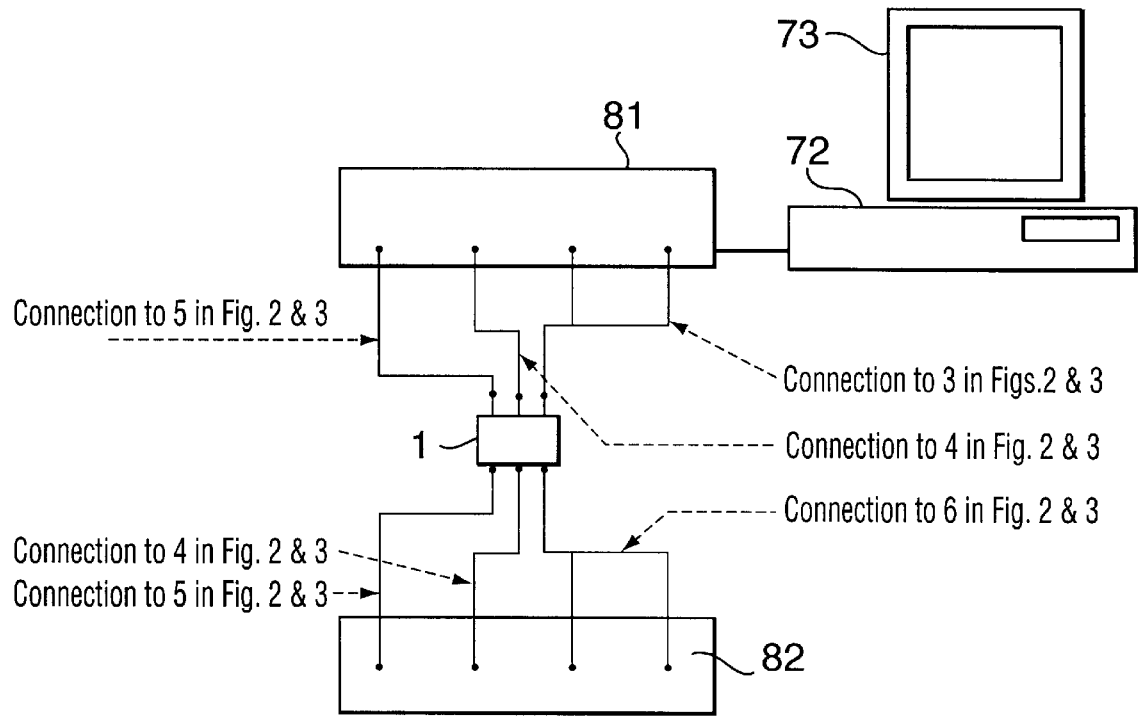

FIGS. 7 and 8 show schematic circuit diagrams for these two sets of measurements. In FIG. 7, the probe 1 includes three electrodes as in FIG. 1, and in FIG. 8 the probe includes four electrodes as in FIG. 2; in each of FIGS. 7 and 8 the probe leads are numbered to correspond with FIGS. 1 and 2. In FIG. 7, leads from the probe 1 are connected to a potentiostat unit 71 which provides the required electrical power. In FIG. 8, selected leads from the probe 1 are connected to each potentiostat 81 and 82, which provide the required electrical power for the two different measurements. In each arrangement, the measurement signals are transferred to a computer unit 72 for processing, and storage, and can be displayed when required on the screen 73.

At a pre-programmed time, a suitable potential is applied between the enzyme and the counter electrodes. The applied potential depends on the cofactor used; for example, when the cofactor is 1,1'-dimethylferrocene, a suitable potential for the enzyme electrode is +0.3V vs. a standard calomel reference electrode. The current flow is then monitored, and, based on the measured current, the sulphide concentration is calculated, displayed and if desired stored in the memory. This calculation is based on pre-calibration of the probe using known sulphide concentrations to provide a calibration chart.

Figure 9:
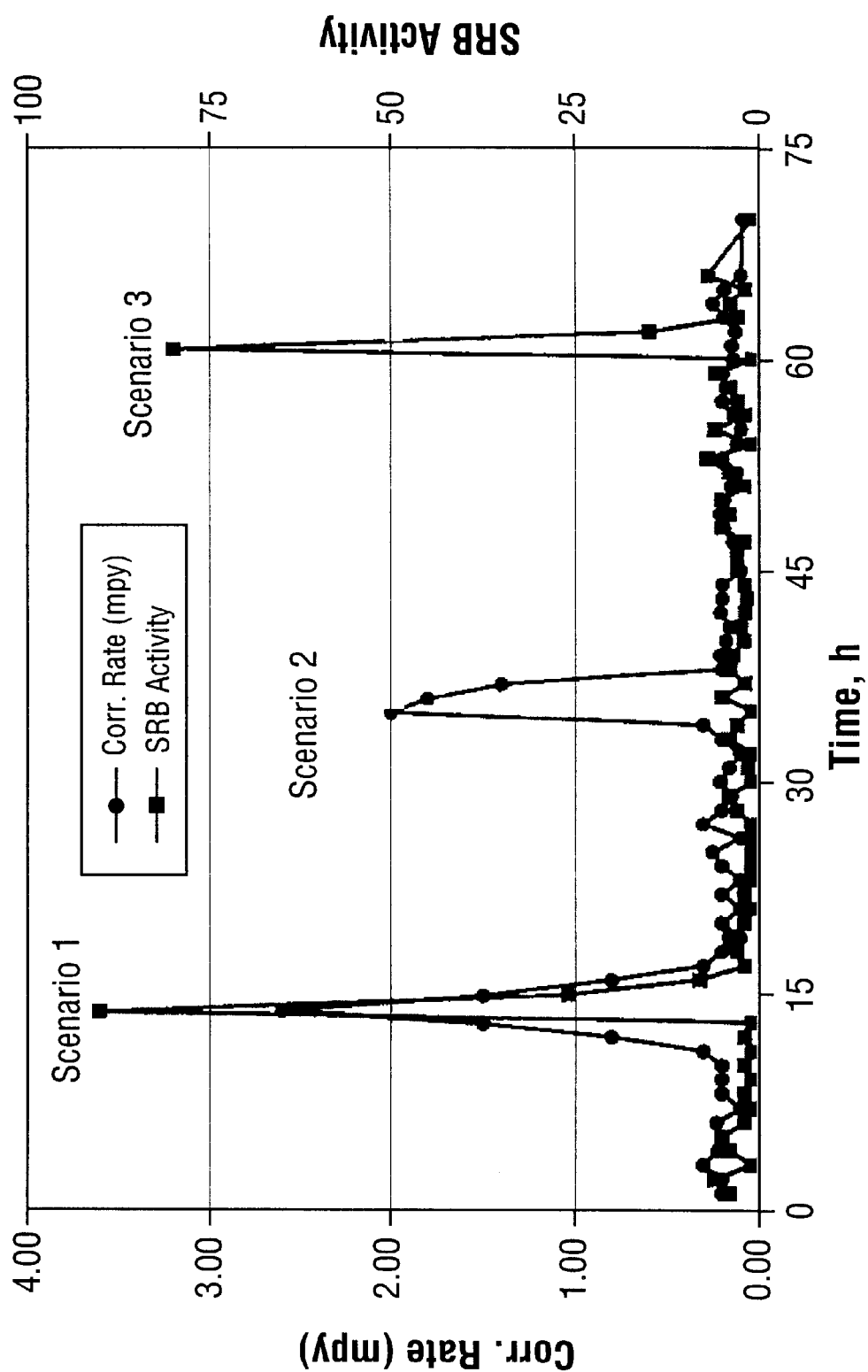
FIG. 9 shows a typical combined plot of SRB activity and derived corrosion rate.

At a different pre-programmed time, a potential scan is carried out, between −20 mV and +20 mV with respect to the corrosion potential, at a scan rate of 0.1 mV/sec, starting at −20 mV. From the slope of the linear relationship between current and potential the corrosion rate in mm/year is calculated, displayed, and if desired stored in the memory. A typical set of results is shown in FIG. 9. Inspection of FIG. 9 shows that the biological activity probe of this invention is capable of identifying four different possibilities:

(1) microbiological activity resulting in microbiologically influenced corrosion;
(2) microbiological activity not resulting in microbiologically influenced corrosion;
(3) microbiological inactivity, coupled with non-microbiologically influenced corrosion; and
(4) microbiological inactivity, and no corrosion.

The biological activity probe of this invention has several other applications, including sulphide determinations in other aqueous environments. It can be used with metal objects comprising a wide range of structures under an almost equally wide range of conditions. The probe is thus potentially useful not only for metallic structures which are risk of corrosion but also non-metallic structures, the performances which are at risk to biofilm formation. Thus although it is of use primarily for metallic structures, such as steel and other iron alloys, copper, aluminium, and nickel, it is also of use for plastic structures, such as pipes, especially if these structures use metal connectors to link parts, such the lengths of a pipe run. The probe can be used in any situation where biofilm formation is possible, and there is a surface to be contaminated. It is thus of use not only when buried adjacent to a pipe, but also where there is enough water, either fresh or saline, or enough humidity, to permit biofilm formation, and enough fluid phase present for the probe to work.

Although there is some range of choice for the reference and counter electrodes, the corrosion electrode should be made from the same metal as the structure being monitored. If the corrosion electrode is not of the same metal as the structure, then the readings will not be directly related to the corrosion behaviour of the structure. The reference and counter electrodes are also conveniently fabricated from the same metal as the corrosion electrode; they can also be made from a suitable grade of graphite.

For many structures, steps are taken both to prevent corrosion, and to minimise biofilm formation. In many cases these steps might interfere with the operation of the biological activity probe of this invention. For example, biocides will possibly kill the microorganism in a probe; the probe will cease to function as required, and the only information it will provide is that the biocide is effective.

In the above description it is assumed that the biological activity probe is more or less continuously connected to a data handling system. For field use, the probe can be remotely powered by batteries or solar cells, and be coupled to a suitable programming device for taking readings including a suitable memory. The data in the memory can then be retrieved by any suitable method.

What is claimed is:

1. A probe for monitoring the activity of sulphide producing microorganisms in the environment of a structure incorporating a metal including:
   (1) an enzyme electrode;
   (2) a counter electrode;
   (3) a reference electrode; and
   (4) a corrosion electrode;
which are all connectable to a suitable electrical system for both data acquisition, data storage, and data retrieval, wherein:
   the enzyme electrode comprises an immobilised source of sulfide oxidase enzyme, together with a cofactor, immobilised in a water permeable non-conducting binder on a biologically inert electrically conducting substrate;
   the cofactor comprises an artificial mediator that replaces oxygen under an aerobic conditions;
   the counter electrode comprises a biologically inert electrically conducting electrode;
   the reference electrode comprises a biologically inert electrically conducting electrode; and
   the corrosion electrode comprises a metal electrode.

2. A probe according to claim 1 wherein the immobilised source of sulphide oxidase enzyme is chosen from the group consisting of an immobilised *Thiobacillus thioparus* microorganism, and a sulphide oxidase enzyme preparation obtained from a *Thiobacillus thioparus* species.

3. A probe according to claim 2 wherein the immobilised source of sulphide oxidase enzyme is an immobilised microorganism of the *Thiobacillus thioparus* species.

4. A probe according to claim 1 wherein the cofactor is chosen from the group consisting of pyocyanine, phenazine metasulphate, 1,2-naphthaquinone, 2,6-dichlorophenolindophenol, tetracyanoquinodimethane, 1,4-benzoquinone, the compound $Ru(NH_3)_5pyridinium(PF_6)$, chlomil, potassuin ferricyanide, N,N,N',N'-tetramethyl-p-phenylenediamine, ferrocene monocarboxylic acid, tetrathiafulvene, ferrocene and 1,1'-dimethyl ferrocene.

5. A probe according to claim 4 wherein the cofactor is chosen from 1,1'-dimethyiferrocene and ferrocene.

6. A probe according to claim 4 wherein the cofactor is 1,1'-dimethylferrocene.

7. A probe according to claim 1 wherein the counter electrode and the corrosion electrode are of the same material.

8. A probe according to claim 1 wherein the counter electrode and the corrosion electrode are not of the same material.

9. A probe according to claim 1 wherein the counter electrode is chosen from the group consisting of a steel electrode and a graphite electrode.

10. A probe according to claim 1 wherein the reference electrode is chosen from the group consisting of a graphite electrode, a stainless steel electrode, a carbon steel electrode; a standard calomel electrode (SCE), a copper/copper sulphate electrode, and a silver/silver chloride electrode.

11. A probe according to claim 1 wherein the electrodes are mounted within a protective outer shell having an opening at its first end for the electrode active surfaces, and a provision for electrical connections to the electrodes at its second end, and wherein the electrodes are separated from each other within the shell by a biologically inert insulating material.

* * * * *